United States Patent [19]

Dzula

[11] Patent Number: 4,691,168
[45] Date of Patent: Sep. 1, 1987

[54] HIGH PURITY WATER CALIBRATING DEVICE

[75] Inventor: Gregory Dzula, North Caldwell, N.J.

[73] Assignee: Beckman Industrial Corporation, Cedar Grove, N.J.

[21] Appl. No.: 791,126

[22] Filed: Oct. 24, 1985

[51] Int. Cl.⁴ ............................................. G01N 27/02
[52] U.S. Cl. ................................... 324/439; 204/409; 73/1 R; 324/438
[58] Field of Search ........................ 324/439, 438, 450; 204/1 T, 409, 433; 210/662; 73/1 R, 1 G

[56] References Cited

U.S. PATENT DOCUMENTS 3,839,162  10/1974  Ammer .............................. 210/662 X
3,897,213   7/1975  Stevens et al. ..................... 210/662 X
4,384,925   5/1983  Stetter et al. ...................... 204/409 X
4,445,091   4/1984  Küsebauch et al. ............. 324/439 X

FOREIGN PATENT DOCUMENTS 2937227  12/1980  Fed. Rep. of Germany ...... 324/438

Primary Examiner—Reinhard J. Eisenzopf
Assistant Examiner—Jack B. Harvey
Attorney, Agent, or Firm—Daniel H. Bobis

[57] ABSTRACT

Apparatus for calibrating a conductivity instrument having a conductivity cell and a conductivity measuring instrument operatively associated with the conductivity cell, includes a conduit for supplying high purity water to be measured; a first flow line for supplying the high purity water from the conduit to the conductivity cell; a second flow line for supplying the high purity water from the conduit to the conductivity cell; a mixed bed ion exchanger in the second flow line for de-ionizing the high purity water flowing through the second flow line; and a valve which selectively supplies the high purity water to the conductivity cell, from either the first flow line to provide a conductivity measurement of the high purity water or the second flow line to calibrate the conductivity cell.

6 Claims, 1 Drawing Figure

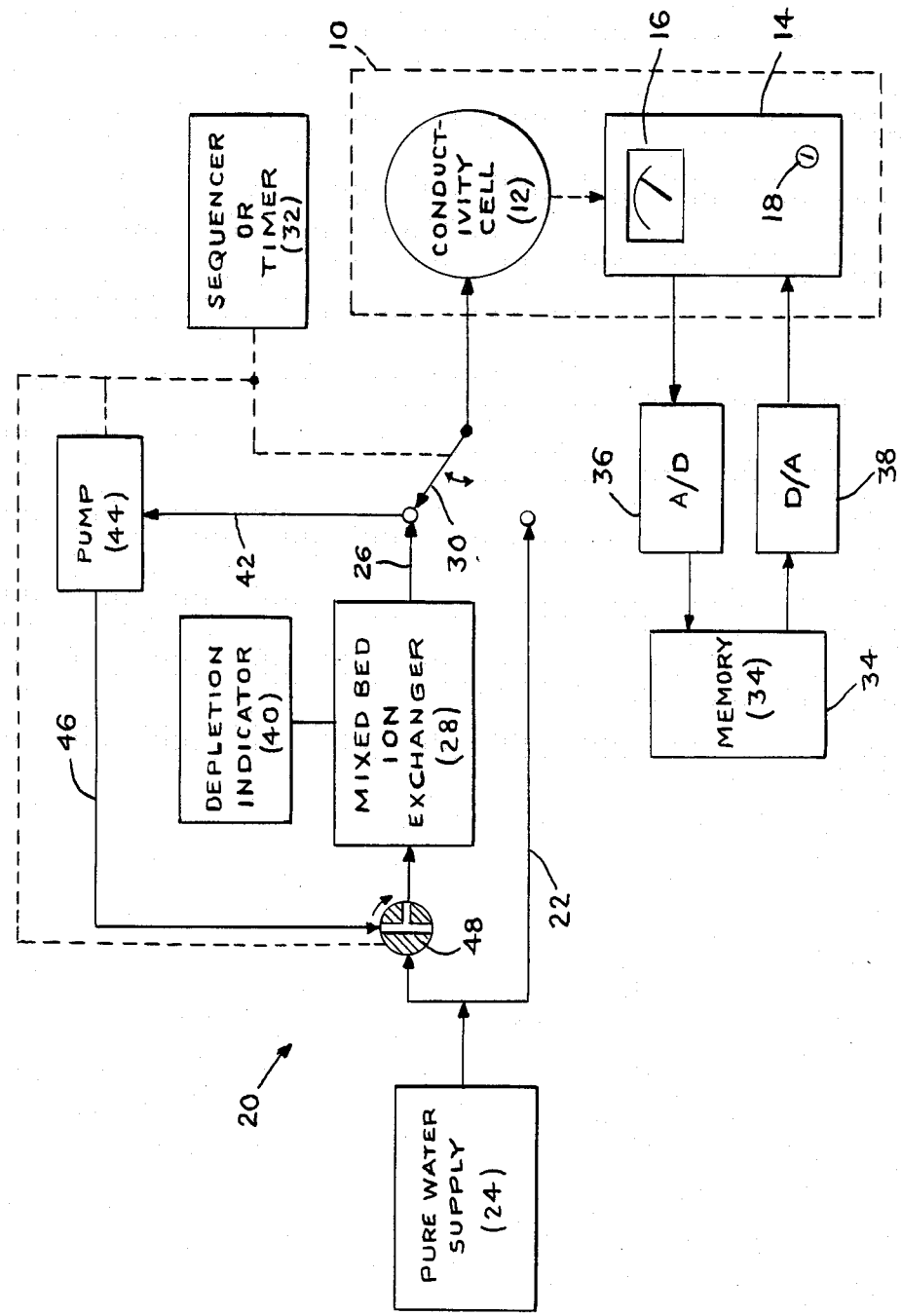

HIGH PURITY WATER CALIBRATING DEVICE

BACKGROUND OF THE INVENTION

The present invention relates generally to conductivity instruments and, more particularly, is directed to apparatus for calibrating a conductivity instrument used to measure the conductivity of pure water.

In many instances, it is necessary to utilize high purity water. In order to ensure that the water is of sufficient purity, conductivity instruments are provided for measuring the conductivity of the high purity water. These instruments are extremely sensitive, producing conductivity measurements having a sensitivity of more than one part in sixteen thousand, that is, at least $10^{-4}$. It therefore becomes extremely important that the conductivity cell of the calibrating instrument be calibrated prior to such conductivity measurements.

The greatest problem with the measurement of conductivity is the determination of the cell constant. Even if the cell constant is determined accurately when manufactured, it can only reliably be calibrated to within 0.5–1.0%. When placed in use, the value of the cell constant can change for various reasons, including the proximity of other metals, and usage. Further, the surfaces of the electrodes of the conductivity cell become contaminated after use and increase the cell constant.

Various systems have been devised for calibrating or standardizing test cells of a monitoring system. For example, U.S. Pat. No. 4,151,255, discloses a method for standardizing test cells of a monitoring system. In normal operation, a sample is fed into a vessel which contains three electrodes. One electrode is a glass electrode for measuring the pH of the sample fluid contained within the vessel. Another electrode is a reference electrode for use in such measurement and the third electrode is a temperature sensing electrode which compensates for variations of temperature of the sample fluid fed to the vessel.

In order to assure that the monitoring and measuring analyzer provides an accurate measurement of the pH of the fluid sample from the process, a buffer solution of known pH is fed to the vessel of the test chamber. However, this patent requires two buffer storage means for holding two different standard buffer solutions for use in standardizing the reading of the pH measuring means during intermittant buffer standardization. The storage of different buffer solutions, and the necessary supply lines and valves associated therewith, makes this apparatus relatively expensive and complicated.

U.S. Pat. No. 4,445,091 discloses a system for determining the pH value of deionized cooling water by conductivity measurements, which includes a main loop and at least one parallel loop which includes an ion exchanger so that the two conductivity cells can be utilized by different measurement to provide a true measurement of the deionized water in the system. These ion exchangers fix the standard for one conductivity cell so that the measured difference between the two conductivity cells will correspond to the actual pH value of the deionized water in the system being measured. This patent, however, does not supply the calibrated water and water to be measured to the same conductivity cell. Rather, two different conductivity cells are used and an adjustment must be made based on calibration of only one of the cells, thereby making this system relatively complicated, and expensive, because of the additional conductivity cell that is required.

U.S. Pat. No. 4,357,143 shows a parallel flow system in which one portion of the sample water is passed through an ion exchange resin column and then the two samples are passed to a detection cell which has two ion specific electrodes therein connected through conventional bridge circuitry. The differential between the two cells is measured for the system. Thus, the use of two cells in this patent is similar to that of U.S. Pat. No. 4,445,091.

Attention is also directed to U.S. Pat. Nos. 1,684,645; 3,451,403; and 4,473,458.

OBJECTS AND SUMMARY OF THE INVENTION

Accordingly, it is an object of the present invention to provide apparatus for calibrating the conductivity cell of a high purity water conductivity instrument;

It is another object of the present invention to provide apparatus for easily and readily calibrating a high purity water conductivity instrument prior to measurement.

It is still another object of the present invention to provide apparatus for calibrating a high purity water conductivity instrument that does not require the storage of separate calibrating solutions.

It is yet another object of the present invention to provide apparatus for calibrating a high purity water conductivity instrument by using a single conductivity cell.

It is a further object of the present invention to provide apparatus for calibrating a high purity water conductivity instrument with the same high purity water that is to be measured.

In accordance with an aspect of the present invention, apparatus for calibrating a conductivity instrument having a conductivity cell and a conductivity measuring instrument operatively associated with the conductivity cell, includes:
  (a) conduit means for supplying pure water to be measured by the conductivity instrument;
  (b) first flow line means for supplying the pure water from the conduit means to the conductivity cell;
  (c) second flow line means for supplying the pure water from the conduit means to the conductivity cell;
  (d) ion exchange means in the second flow line means for de-ionizing the pure water flowing through the second flow line means; and
  (e) valve means for selectively supplying the pure water to the conductivity cell, from one of:
    (i) the first flow line means to provide a conductivity measurement of the pure water; and
    (ii) the second flow line means to calibrate the conductivity cell.

In accordance with another aspect of the present invention, a method for calibrating a conductivity instrument having a conductivity cell and a conductivity measuring instrument operatively associated with the conductivity cell, includes the steps of:
  (a) supplying pure water to be measured by the conductivity instrument to conduit means;
  (b) supplying the pure water from the conduit means to first flow line means;
  (c) supplying the pure water from the conduit means to second flow line means;
  (d) de-ionizing the pure water flowing through the second flow line means by ion exchange means; and (e) selectively supplying the pure water to the conductivity cell, from one of:
(i) the first flow line means to provide a conductivity measurement of the pure water; and
(ii) the second flow line means to calibrate the conductivity cell.

The above and other, objects, features and advantages of the present invention will become readily apparent from the following detailed description thereof which is to be read in connection with the accompanying drawings.

BRIEF DESCRIPTION OF THE DRAWINGS

The only FIGURE of the drawings is a schematic flow diagram of apparatus for calibrating a high purity water conductivity instrument according to the present invention.

DETAILED DESCRIPTION OF THE PREFERRED EMBODIMENTS

Referring to the single FIGURE of the drawings, a conductivity instrument 10 is shown for measuring the conductivity of high purity water. The conductivity instrument 10 includes a conductivity cell 12 to which the high purity water is supplied and a conductivity measuring instrument 14 connected to conductivity cell 12 for determining the conductivity of the high purity water. Conductivity cell 12 is a conventional device and includes a vessel with a plurality of electrodes therein which are sensitive to the conductivity of the high purity water. The electrodes supply an electrical signal to the conductivity measuring instrument 14, which is also conventional. Conductivity measuring instrument 14 includes a display 16 and a control knob 18 for adjusting the display output. Display 16 may be an analog display, as shown, including a pointer and scale, or alternatively, may be a digital display.

In accordance with the present invention, apparatus 20 for calibrating conductivity instrument 10 includes a first flow line 22 supplied with high purity water from a high purity water supply 24 and a second flow line 26 also supplied with such high purity water from high purity water supply 24. A mixed bed ion exchanger 28 is connected in second flow line 26 so as to de-ionize the high purity water flowing therethrough.

Apparatus 20 further includes a valve, shown schematically at 30, which selectively supplies the high purity water from first flow line 22 or second flow line 26 to conductivity cell 12. In this regard, valve 30 can be manually actuated, or automatically actuated by a servo control 32, as shown.

In the basic operation, valve 30 is actuated to supply high purity water from second flow line 26 to conductivity cell 12. Thus, the high purity water from supply 24 is supplied through mixed bed ion exchanger 28 where it is de-ionized, and then supplied to conductivity cell 12. To calibrate conductivity instrument 10, conductivity measuring instrument 14 is then adjusted by control knob 18 such that display 16 has a reading of 18.3 Megohms which is the theoretical maximum specific conductivity of pure water. Thereafter, valve 30 is rotated such that high purity water from high purity water supply 24 is supplied through first flow line 22 to conductivity cell 12, whereby conductivity measuring instrument 14 will then accurately read the purity of the water from high purity water supply 24.

In this regard, the same water that is to be measured is used to calibrate conductivity instrument 10. At the same time, only a single conductivity cell 12 is required for such calibration, thereby reducing the complexity and cost of the apparatus.

Various modifications can be made to the present invention by one of ordinary skill in the art. For example, valve 30 may be an electromagnetically operated valve which is controlled by a sequencing or timing system 32. The sequencing or timing system 32 will provide automatic calibration by periodically controlling valve 30 to supply high purity water through mixed bed ion exchanger 28 to conductivity cell 12.

In addition, the calibrated value could be stored in an electronic or other suitable memory unit 34, whereby subsequent or later readings can be compared with this calibrated reading. Memory unit 34 may simply be a capacitor that is charged to a particular voltage, or alternatively, may be more complex and thus include, a digital memory. In this latter device, the calibrated reading from conductivity measuring instrument 14 would be supplied through an analog-to-digital (A/D) converter 36 to memory unit 34, and return from memory unit 34 to conductivity measuring instrument 14 through a digital-to-analog (D/A) converter 38, as shown. In such case, suitable READ/WRITE circuitry would be provided for accessing the information in memory 34.

Still further, a depletion indicator 40 can be associated with the mixed bed ion exchanger 28 to indicate depletion of the mixed bed ion exchange resin therein, to prevent erroneous readings. Depletion indicator 40 may take the form of color indicating resins, or alternatively, may be more complex and include an alarm which is activated when the conductivity readings of water through mixed bed ion exchanger 28 are close to the conductivity readings of water flowing through first flow line 22.

A further improvement upon the apparatus could be the use of a recirculating standardizing scheme, in which the standardized water which has already passed through mixed bed ion exchanger 28 is continuously recirculated back through mixed bed ion exchanger 28 to maintain the water at its highest purity at all times. Specifically, a portion of the high purity water which has passed through mixed bed ion exchanger 26 will flow through first auxiliary flow line 42 to a fluid pump 44 which pumps the fluid through a second auxiliary flow line 46 to the input of mixed bed ion exchanger 28. In such case, a three-way valve 48 can be provided at the input of mixed bed ion exchanger 28 for selectively supplying the fluid thereto from high purity water supply 24 or second auxiliary flow line 46. In this regard, servo control system 32 could be used to actuate pump 44 and to rotate three-way valve 48 at a time when valve 30 is rotated to permit flow between first flow line 22 and conductivity cell 12, as shown.

Further, it is preferable that first flow line 22 and second flow line 26 are placed in close proximity to each other to minimize problems associated with temperature compensation of high purity water.

Having described specific preferred embodiments of the invention with reference to the accompanying drawings, it will be understood that the present invention is not limited to these precise embodiments, and that various changes and modifications may be effected by one of ordinary skill in the art without departing from the scope and spirit of the invention as defined by the appended claims.

What is claimed is:

1. Apparatus for calibrating a conductivity instrument having a conductivity cell and a conductivity measuring instrument operatively associated with said conductivity cell, said apparatus comprising:
   a. conduit means for supplying pure water to be measured by said conductivity instrument;
   b. first flow line means for supplying said pure water from said conduit means to said conductivity cell;
   c. second flow line means for supplying said pure water from said conduit means to said conductivity cell;
   d. ion exchange means in said second flow line means for de-ionizing said pure water flowing through said second flow line means; and
   e. valve means for selectively supplying said pure water to said conductivity cell, from one of:
      i. said first flow line means to provide a conductivity measurement of said pure water; and
      ii. said second flow line means to calibrate said conductivity cell, and
   f. recirculation means connected to said second flow line means for recirculating at least a portion of the pure water flowing through said second flow line means and the ion exchange means to maintain the same at its highest purity at all times.

2. Apparatus according to claim 1; further including servo control means for controlling said valve means to periodically supply said pure water from said second flow line means to said conductivity cell.

3. Apparatus according to claim 1; wherein said conductivity measuring instrument produces a signal corresponding to the conductivity of said pure water supplied to said conductivity cell; and further comprising memory means for storing the signal corresponding to the conductivity of pure water supplied from said second flow line means.

4. A method of calibrating a conductivity instrument having a conductivity cell and a conductivity measuring instrument operatively associated with said conductivity cell, comprising the steps of:
   a. supplying pure water to be measured by said conductivity instrument through conduit means;
   b. supplying said pure water from said conduit means to first flow line means;
   c. supplying said pure water from said conduit means to second flow line means;
   d. de-ionizing said pure water flowing through said second flow line means by ion exchange means; and
   e. selectively supplying the pure water to the conductivity cell, from one of:
      i. said first flow line means to provide a conductivity measurement of said pure water; and
      ii. said second flow means to calibrate said conductivity cell, and
   f. recirculating at least a portion of said pure water through said second flow line means and said ion exchange means to maintain the same at its highest purity.

5. A method according to claim 4; further comprising the step of periodically and automatically, selectively supplying said pure water to said conductivity cell, from one of:
   a. said first flow line means; and
   b. said second flow line means.

6. A method according to claim 4; further comprising the step of storing in memory means a signal corresponding to the measured conductivity of said pure water from said second flow line means.

* * * * *